(12) United States Patent
Sakaguchi et al.

(10) Patent No.: US 10,068,320 B2
(45) Date of Patent: Sep. 4, 2018

(54) IMAGE PROCESSING APPARATUS AND X-RAY DIAGNOSTIC APPARATUS

(71) Applicant: Toshiba Medical Systems Corporation, Otawara-shi (JP)

(72) Inventors: Takuya Sakaguchi, Utsunomiya (JP); Haruki Iwai, Otawara (JP); Ryoichi Nagae, Nasushiobara (JP)

(73) Assignee: Toshiba Medical Systems Corporation, Otawara-shi (JP)

(*) Notice: Subject to any disclaimer, the term of this patent is extended or adjusted under 35 U.S.C. 154(b) by 74 days.

(21) Appl. No.: 15/133,788

(22) Filed: Apr. 20, 2016

(65) Prior Publication Data

US 2016/0307304 A1    Oct. 20, 2016

(30) Foreign Application Priority Data

Apr. 20, 2015 (JP) ................. 2015-086205

(51) Int. Cl.
*G06T 5/00* (2006.01)
*A61B 6/00* (2006.01)
*G06T 11/00* (2006.01)

(52) U.S. Cl.
CPC ............. *G06T 5/008* (2013.01); *A61B 6/481* (2013.01); *A61B 6/507* (2013.01); *A61B 6/5258* (2013.01); *G06T 11/005* (2013.01); *G06T 11/008* (2013.01); *G06T 2207/10124* (2013.01); *G06T 2207/10132* (2013.01); *G06T 2207/30101* (2013.01)

(58) Field of Classification Search
CPC ........... G06T 2207/30101; G06T 5/008; G06T 11/005; G06T 11/008; G06T 2207/10124; G06T 2207/10132; A61B 6/481; A61B 6/507; A61B 6/5258
See application file for complete search history.

(56) References Cited

U.S. PATENT DOCUMENTS 5,908,387 A * 6/1999 LeFree ................. A61B 5/1076
                                                        600/425
7,496,175 B2    2/2009 Sakaguchi et al.
(Continued)

FOREIGN PATENT DOCUMENTS

JP    2008-136800    6/2008
JP    2012-115651    6/2012

OTHER PUBLICATIONS

Sakaguchi et al. "Development of a theory for generating regional cardiac perfusion images during coronary angiography in the coronary angiography lab." The international journal of cardiovascular imaging 30.1 (Oct. 2013): 9-19.*

(Continued)

*Primary Examiner* — Katrina Fujita
(74) *Attorney, Agent, or Firm* — Oblon, McClelland, Maier & Neustadt, L.L.P.

(57) ABSTRACT

An image processing apparatus according to an embodiment includes processing circuitry. The processing circuitry is configured to acquire correction information on a luminance value of a contrast image, based on concentration of a contrast material and thickness of the contrast material in a projection direction in a device that is inserted into a blood vessel, in the contrast image. The processing circuitry is configured to correct the contrast image using the correction information.

15 Claims, 10 Drawing Sheets

(56) References Cited

U.S. PATENT DOCUMENTS

| | | | |
|---|---|---|---|
| 8,718,347 B2* | 5/2014 | Ichihara | A61B 6/032 378/20 |
| 8,965,085 B2 | 2/2015 | Sakaguchi et al. | |
| 2004/0006268 A1* | 1/2004 | Gilboa | A61B 5/06 600/424 |
| 2006/0241402 A1* | 10/2006 | Ichihara | A61B 6/481 600/425 |
| 2008/0273782 A1* | 11/2008 | Ichihara | A61B 5/0275 382/131 |
| 2014/0100550 A1* | 4/2014 | Zarei Mahmoodabadi | A61B 5/0077 604/510 |
| 2014/0350393 A1* | 11/2014 | Ichihara | A61B 5/029 600/425 |

OTHER PUBLICATIONS

Takuya Sakaguchi, et al., "Development of Calibration Phantoms for Generating Quantitative Perfusion Images Using 2D Angiography Data", IEEE Nucl. Sci. Symp. Med. Imaging Conf. Rec., 2014, 5 pgs.

Jingwu Yao, et al., "Linear Quantification Correction for Myocardial Perfusion Imaging from X-Ray Coronary Angiography", IEEE Nuclear Science Symposium and Medical Imaging Conference Record (NSS/MIC), 2012, 6 pgs.

* cited by examiner

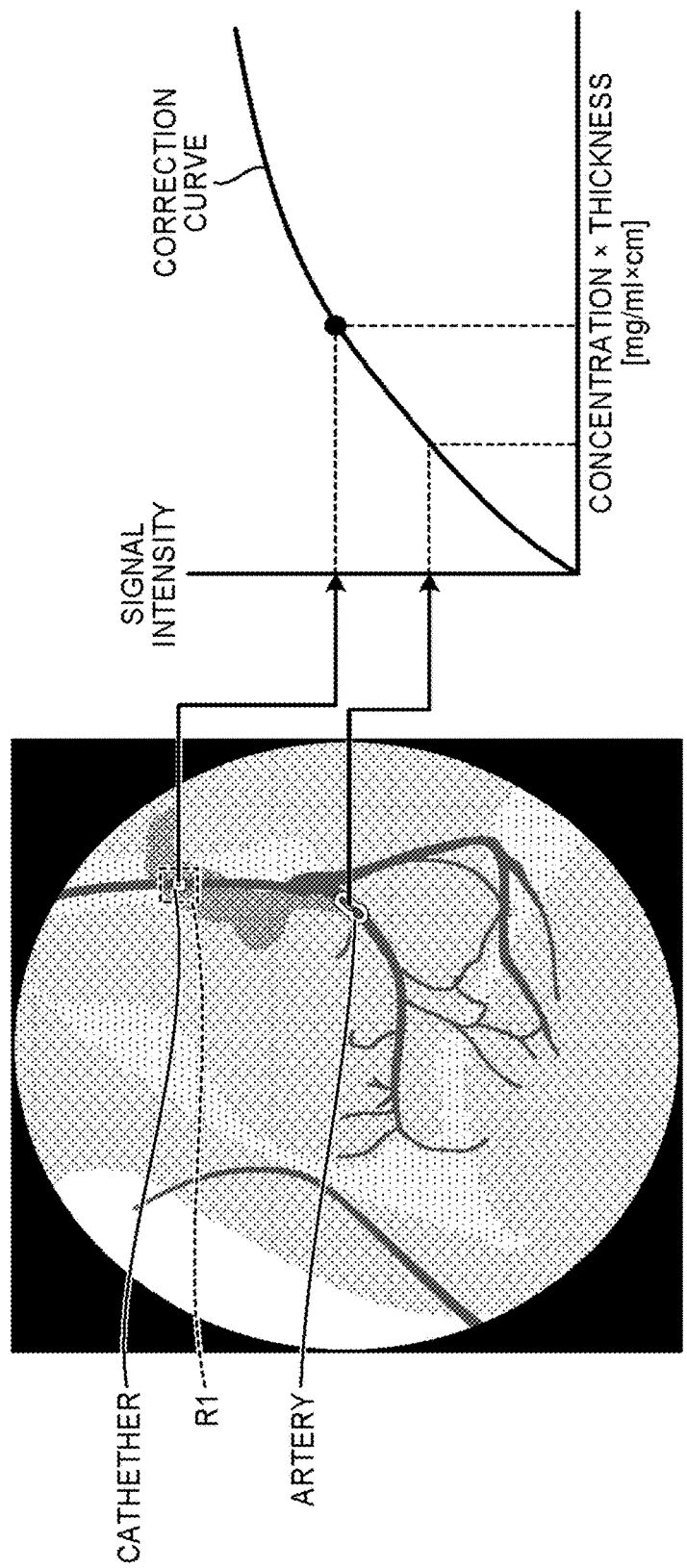

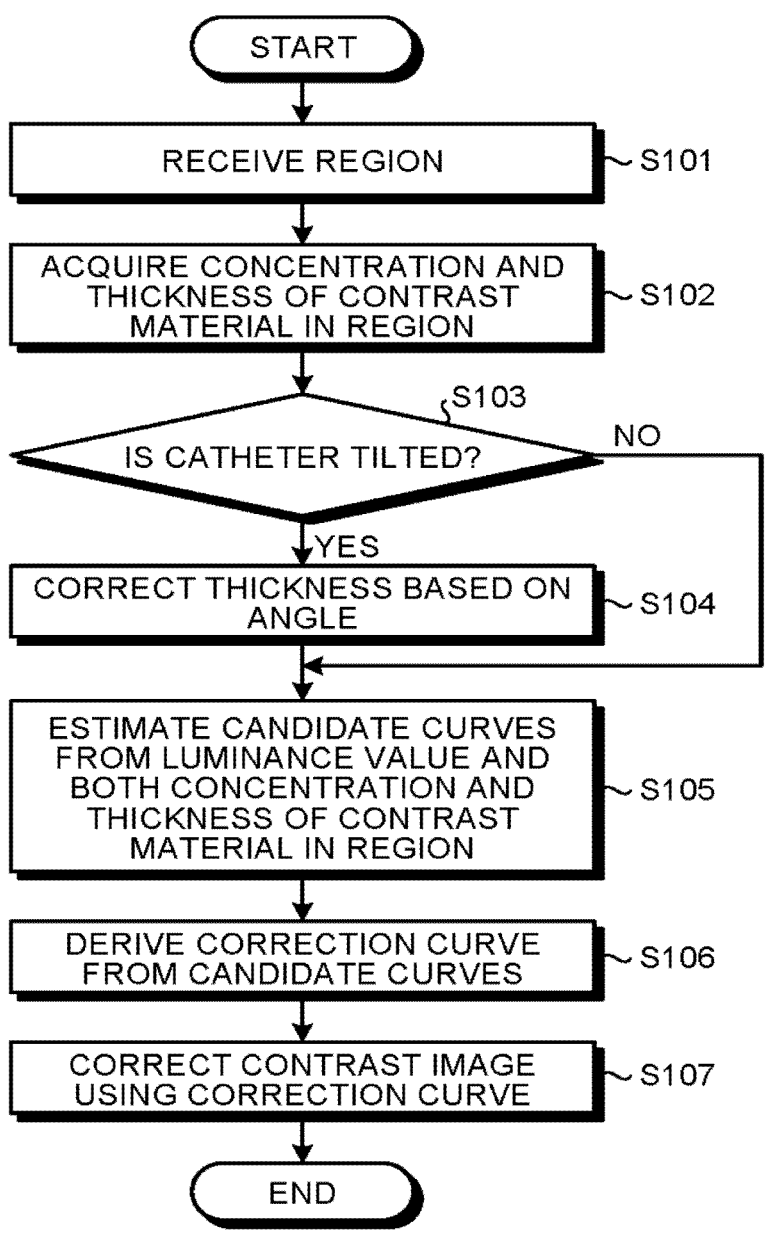

IMAGE PROCESSING APPARATUS AND X-RAY DIAGNOSTIC APPARATUS

CROSS-REFERENCE TO RELATED APPLICATIONS

This application is based upon and claims the benefit of priority from Japanese Patent Application No. 2015-086205, filed on Apr. 20, 2015; the entire contents of which are incorporated herein by reference.

FIELD

Embodiments described herein relate generally to an image processing apparatus and an X-ray diagnostic apparatus.

BACKGROUND

Conventionally, an X-ray diagnostic apparatus has been used for endovascular intervention treatment, for example, using an iodine-based contrast material. In the endovascular intervention treatment, the concentration of the contrast material in a subject may be estimated from an X-ray image obtained by the X-ray diagnostic apparatus. For example, during coronary artery intervention treatment, it is known that the evaluation of perfusion of contrast material into the tissues improves prognosis of patients with ischemic heart disease. Hence, methods for measuring perfusion in a two-dimensional angiographic image have been developed.

In the X-ray diagnostic apparatus, a luminance value (e.g. Signal Intensity) and the concentration of the contrast material in the two-dimensional image are not in a proportional relation, due to scatter, beam hardening, and the like. Thus, to accurately measure perfusion in the two-dimensional angiographic image, the luminance value and the concentration of the contrast material need to be corrected to be in a proportional relation. For example, known correction methods include a method of performing a calibration in advance, a correction method using a phantom, and the like, while the contrast image is obtained. However, in the conventional technology described above, the correction takes time because a complicated calibration is required in advance or a phantom needs to be prepared. Further, it is difficult to perform the correction processing on the contrast image that is already obtained.

BRIEF DESCRIPTION OF THE DRAWINGS

FIG. 7 is a diagram schematically illustrating processing by a correction function according to the first embodiment;

FIG. 10 is a flowchart illustrating a processing procedure of the X-ray diagnostic apparatus according to the first embodiment.

DETAILED DESCRIPTION

According to an embodiment, an image processing apparatus includes processing circuitry. The processing circuitry is configured to acquire correction information on a luminance value of a contrast image, based on concentration of a contrast material and thickness of the contrast material in a projection direction in a device that is inserted into a blood vessel, in the contrast image. The processing circuitry is configured to correct the contrast image using the correction information.

First Embodiment

Figure 1:
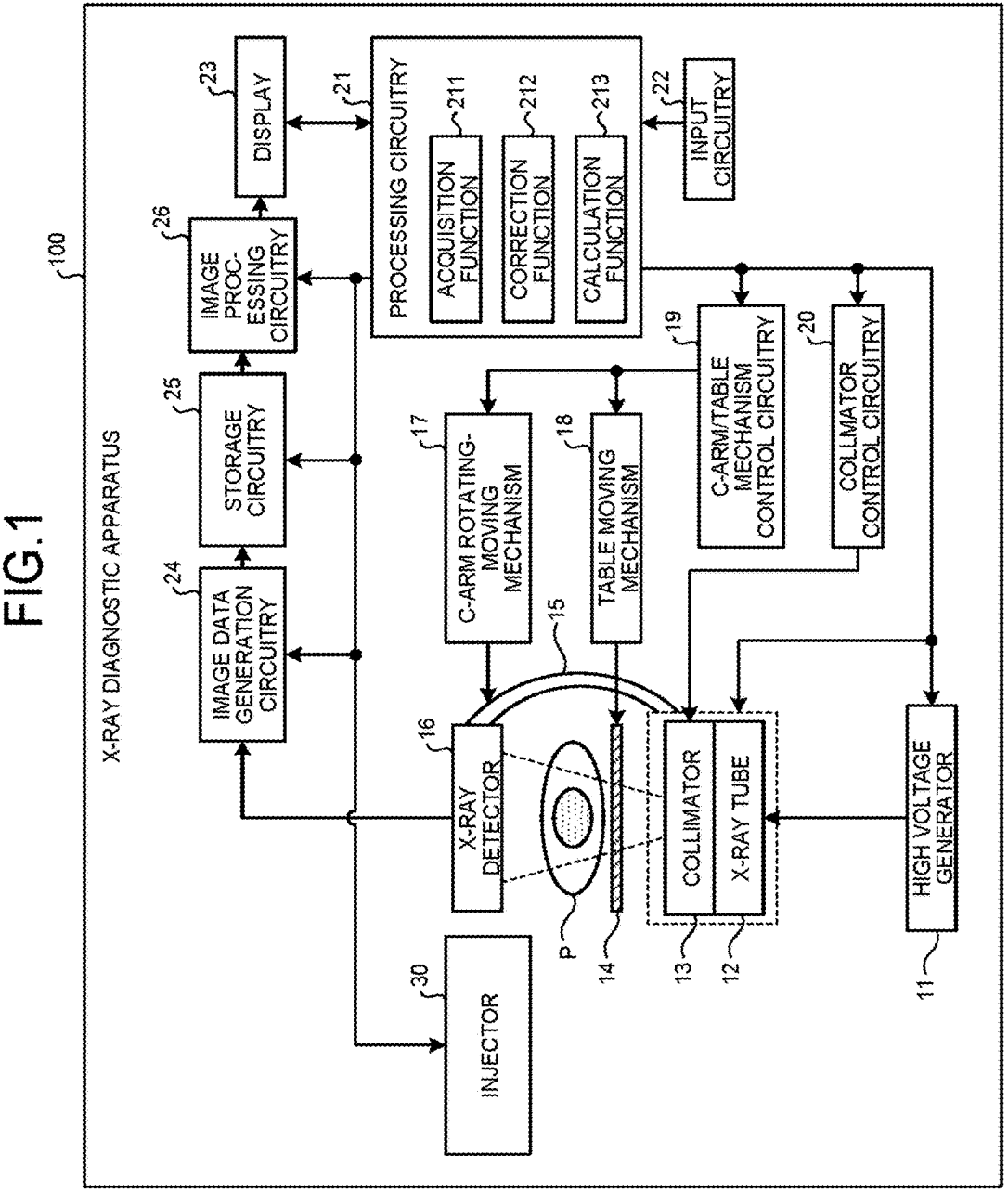
FIG. 1 is a diagram illustrating a configuration example of an X-ray diagnostic apparatus according to a first embodiment.

FIG. 1 is a diagram illustrating a configuration example of an X-ray diagnostic apparatus 100 according to a first embodiment. As illustrated in FIG. 1, the X-ray diagnostic apparatus 100 according to the first embodiment includes a high voltage generator 11, an X-ray tube 12, a collimator 13, a table 14, a C-arm 15, and an X-ray detector 16. The X-ray diagnostic apparatus 100 according to the first embodiment also includes a C-arm rotating-moving mechanism 17, a table moving mechanism 18, C-arm/table mechanism control circuitry 19, collimator control circuitry 20, processing circuitry 21, input circuitry 22, and a display 23. The X-ray diagnostic apparatus 100 according to the first embodiment also includes image data generation circuitry 24, storage circuitry 25, and image processing circuitry 26. The X-ray diagnostic apparatus 100 is also connected to an injector 30. As illustrated in FIG. 1, in the X-ray diagnostic apparatus 100, the circuitry is connected to each other. The circuitry transmits and receives various electric signals therebetween, and transmits and receives electric signals to and from the injector 30.

The injector 30 is a device that injects a contrast material into a subject P through an inserted catheter. The contrast material is injected from the injector 30 according to an injection instruction received via the processing circuitry 21, which will be described below. More specifically, the injector 30 injects the contrast material based on an injection start instruction and an injection stop instruction of the contrast material, as well as contrast material injection conditions including the injection speed and the like, received via the processing circuitry 21, which will be described below. It is also possible to start the injection or stop the injection through the injector 30, according to an injection instruction directly input to the injector 30 by an operator.

In the X-ray diagnostic apparatus 100 illustrated in FIG. 1, each of the processing functions is stored in the storage circuitry 25 in the form of a computer-executable program. Each of the C-arm/table mechanism control circuitry 19, the collimator control circuitry 20, the processing circuitry 21, the image data generation circuitry 24, and the image processing circuitry 26 is a processor that can execute a function corresponding to each program, by reading out the program from the storage circuitry 25 and executing the program. In other words, each of the circuitry that reads out each program has a function corresponding to the program that is read out.

For example, the term "processor" used in the above description means a circuit such as a central processing unit (CPU), a graphics processing unit (GPU), an application specific integrated circuit (ASIC), a programmable logic device (such as a simple programmable logic device (SPLD), a complex programmable logic device (CPLD)), and a field programmable gate array (FPGA). The processor executes the function by reading out the program stored in the storage circuit and executing the program. It is also possible to incorporate the program directly into the circuit of the processor, instead of storing the program in the storage circuit. In this case, the processor executes the function by reading out the program incorporated into the circuit and executing the program. In the present embodiment, each processor may be configured as a single circuit, or a single processor may include a plurality of independent circuits to execute the functions.

Under the control of the processing circuitry 21, the high voltage generator 11 generates high voltage, and supplies the generated high voltage to the X-ray tube 12. The X-ray tube 12 generates X-rays using the high voltage supplied from the high voltage generator 11.

Under the control of the collimator control circuitry 20, the collimator 13 narrows down the X-rays generated by the X-ray tube 12, so that a region of interest of the subject P is selectively irradiated with the X-rays. For example, the collimator 13 includes four slidable collimator blades. Under the control of the collimator control circuitry 20, the collimator 13 narrows down the X-rays generated by the X-ray tube 12 and irradiates the subject P with the X-rays, by sliding the collimator blades. The table 14 is a bed on which the subject P is placed, and is arranged on top of a platform, which is not illustrated. The subject P is not included in the X-ray diagnostic apparatus 100.

The X-ray detector 16 detects the X-rays that have transmitted through the subject P. For example, the X-ray detector 16 includes detection elements arranged in a matrix. Each of the detection elements converts the X-rays that have transmitted through the subject P into electric signals, accumulates the electric signals, and transmits the accumulated electric signals to the image data generation circuitry 24.

The C-arm 15 holds the X-ray tube 12, the collimator 13, and the X-ray detector 16. With the C-arm 15, the X-ray tube 12 and the collimator 13 are arranged so as to face the X-ray detector 16 interposing the subject P therebetween. In FIG. 1, the X-ray diagnostic apparatus 100 is a single plane X-ray diagnostic apparatus. However, the embodiment is not limited thereto, and a biplane X-ray diagnostic apparatus may also be used.

The C-arm rotating-moving mechanism 17 is a mechanism for rotating and moving the C-arm 15. The table moving mechanism 18 is a mechanism for moving the table 14. Under the control of the processing circuitry 21, the C-arm/table mechanism control circuitry 19 adjusts the rotation and movement of the C-arm 15, and the movement of the table 14, by controlling the C-arm rotating-moving mechanism 17 and the table moving mechanism 18. Under the control of the processing circuitry 21, the collimator control circuitry 20 adjusts the opening angle of the collimator blades in the collimator 13. Consequently, the collimator control circuitry 20 controls the irradiation range of the X-rays applied to the subject P.

The image data generation circuitry 24 generates image data using the electric signals converted from the X-rays by the X-ray detector 16, and stores the generated image data in the storage circuitry 25. For example, the image data generation circuitry 24 generates image data, by carrying out a current-voltage conversion, an analog-digital (A-D) conversion, and a parallel-serial conversion on the electric signals received from the X-ray detector 16. For example, the image data generation circuitry 24 generates image data (mask image) captured when the contrast material is not injected, and image data (contrast image) captured when the contrast material is injected. The image data generation circuitry 24 then stores the generated mask image and contrast image in the storage circuitry 25.

The storage circuitry 25 receives and stores therein the image data generated by the image data generation circuitry 24. For example, the storage circuitry 25 stores therein the image data of the subject P before and after the contrast material is injected. The storage circuitry 25 also stores therein programs corresponding to various functions read out and executed by the circuitry illustrated in FIG. 1. For example, the storage circuitry 25 stores therein a program corresponding to an acquisition function 211, a program corresponding to a correction function 212, and a program corresponding to a calculation function 213 that are read out and executed by the processing circuitry 21.

The image processing circuitry 26 performs various types of image processing on the image data stored in the storage circuitry 25. For example, the image processing circuitry 26 reads out the mask image and the contrast image stored in the storage circuitry 25, and generates a differential image by performing subtraction (log subtraction).

The input circuitry 22 is implemented by using a trackball, a switch button, a mouse, a keyboard, and the like, so as to set a predetermined region (such as a catheter region). The input circuitry 22 is connected to the processing circuitry 21. The input circuitry 22 converts an input operation received from the operator to an electric signal, and outputs the electric signal to the processing circuitry 21.

The display 23 displays a graphical user interface (GUI) for receiving an instruction from the operator, a differential image generated by the image processing circuitry 26, and the like.

The processing circuitry 21 controls the overall operation of the X-ray diagnostic apparatus 100. The processing circuitry 21 executes various types of processing, by reading out the programs corresponding to various processing functions for controlling the entire device from the storage circuitry 25, and executing the programs. For example, the processing circuitry 21 controls the high voltage generator 11 according to the instruction of the operator transferred from the input circuitry 22. The processing circuitry 21 then controls the amount of X-rays applied to the subject P and turning on and turning off of the high voltage generator 11, by adjusting the voltage supplied to the X-ray tube 12. Also, for example, the processing circuitry 21 controls the C-arm/table mechanism control circuitry 19 according to the instruction of the operator, and adjusts the rotation and movement of the C-arm 15 and the movement of the table 14. Further, for example, the processing circuitry 21 controls the collimator control circuitry 20 according to the instruction of the operator, and controls the irradiation range of the X-rays applied to the subject P, by adjusting the opening angle of the collimator blades in the collimator 13.

Furthermore, the processing circuitry 21 controls image data generation processing of the image data generation circuitry 24, image processing of the image processing circuitry 26, analysis processing, or the like according to the instruction of the operator. The processing circuitry 21 also controls the display 23 so that the GUI for receiving the instructions of the operator, the image stored in the storage circuitry 25, and the like are displayed thereon. The processing circuitry 21 further controls the injection timing of the contrast material, by transmitting a contrast material injection start signal and a contrast material injection stop signal to the injector 30.

An example of the configuration of the X-ray diagnostic apparatus 100 is described as above. With the configuration as described above, the X-ray diagnostic apparatus 100 according to the present embodiment can easily correct the contrast image, by the processing of the processing circuitry 21, which will be described in detail below. As described above, the luminance value and the concentration of the contrast material in the two-dimensional contrast image are not in a proportional relation. Thus, for example, to accurately measure perfusion, the luminance value and the concentration of the contrast material need to be corrected to be in a proportional relation. Consequently, in the present embodiment, the contrast image is easily corrected by only using the contrast image, without performing the complicated calibration correction or the correction using a phantom of the conventional technology.

Figure 2:
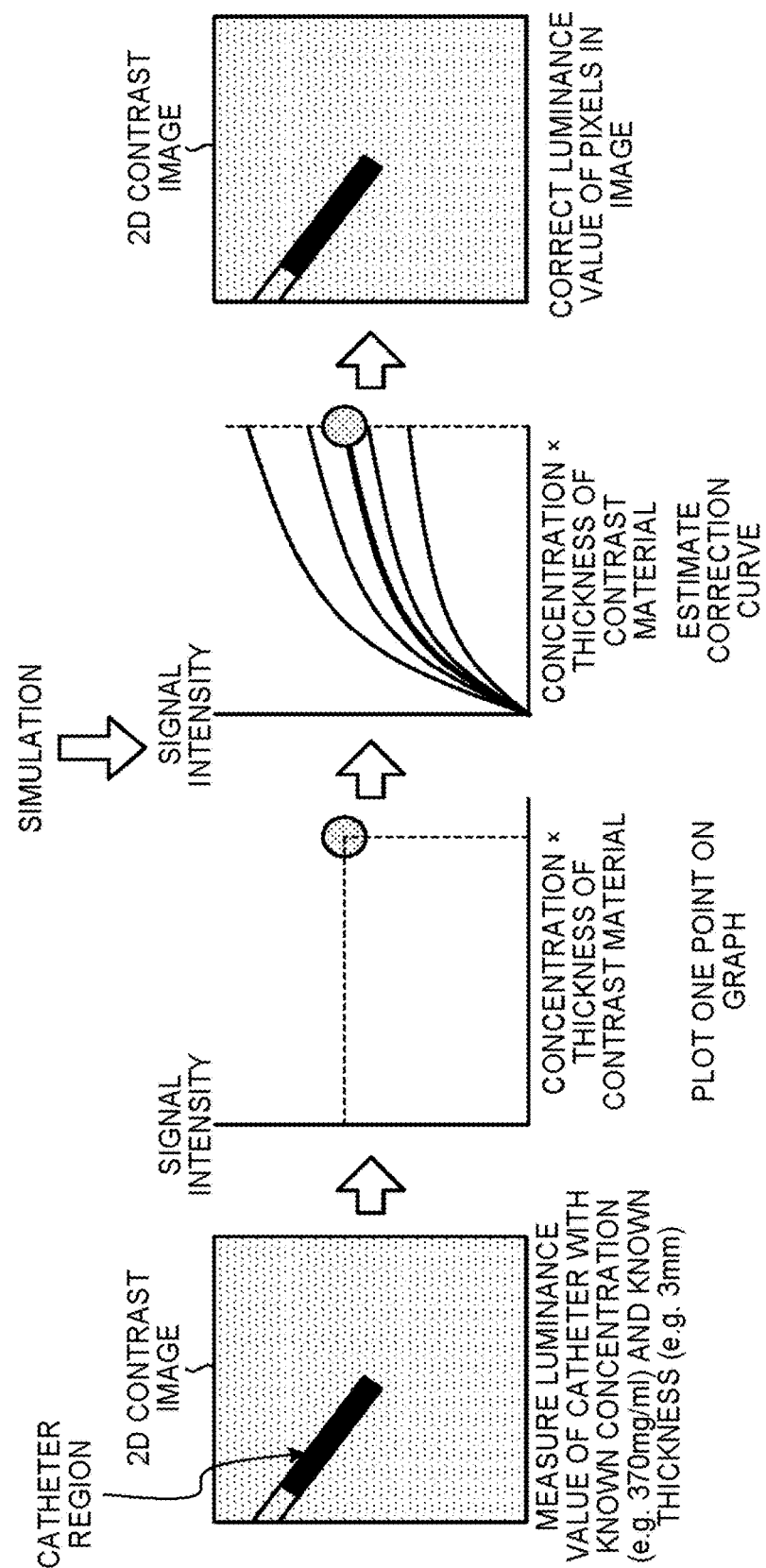
FIG. 2 is a diagram for explaining the outline of processing by the X-ray diagnostic apparatus according to the first embodiment.

More specifically, the X-ray diagnostic apparatus 100 according to the first embodiment estimates a correction curve indicating the relation between the concentration of the contrast material and the luminance value in the contrast image, using the luminance value of a region in which the concentration and thickness of the contrast material in the two-dimensional contrast image are known. The X-ray diagnostic apparatus 100 then corrects the luminance value of each pixel in the contrast image, by using the estimated correction curve. FIG. 2 is a diagram for explaining the outline of processing by the X-ray diagnostic apparatus 100 according to the first embodiment. For example, as illustrated in FIG. 2, a two-dimensional contrast image often includes a catheter. The concentration of the contrast material and the size of the catheter used for obtaining the contrast image are known. In other words, the luminance value of the catheter region in the contrast image is a value based on the contrast material the thickness of which is equivalent to that of the catheter in the projection direction, and is not diluted.

For example, as illustrated in FIG. 2, the X-ray diagnostic apparatus 100 measures the luminance value of the catheter region in which the concentration (e.g. 370 mg/ml) and the thickness (e.g. 3 mm) of the contrast material in the contrast image (differential image) are known. The X-ray diagnostic apparatus 100 then simulates and estimates a correction curve from the relation between the luminance value and both the concentration and thickness of the contrast material being measured. For example, as illustrated in FIG. 2, the X-ray diagnostic apparatus 100 plots the measured luminance value on a graph in which the horizontal axis is the "concentration×thickness of the contrast material", and the vertical axis is the "luminance value of the differential image". Then, the X-ray diagnostic apparatus 100 estimates the curve that passes through the plotted point as the correction curve. The curve indicating the relation between the luminance value and both the concentration and thickness of the contrast material in the contrast image (differential image) depends on beam quality and scatter of the X-rays. Hence, the X-ray diagnostic apparatus 100 simulates and estimates the correction curve while changing the conditions on the beam quality and scatter of the X-rays. The details of how to estimate the correction curve will be described below.

The X-ray diagnostic apparatus 100 corrects the luminance value of each pixel in the contrast image, by using the estimated correction curve. For example, the X-ray diagnostic apparatus 100 corrects the contrast image, by calculating the value of the "concentration×thickness of the contrast material" corresponding to the luminance value of each pixel in the contrast image using the correction curve, and setting the calculated value as the luminance value of each pixel. The above embodiment will now be described in detail. In the X-ray diagnostic apparatus 100 according to the first embodiment, the correction processing is performed on the contrast image described above, when the processing circuitry 21 reads out the programs corresponding to the acquisition function 211, the correction function 212, and the calculation function 213 illustrated in FIG. 1, from the storage circuitry 25, and executes the programs. It is to be understood that the acquisition function 211, the correction function 212, and the calculation function 213 illustrated in FIG. 1 each corresponds to acquisition, correction, and calculation in the claims.

The acquisition function 211 acquires correction information on the luminance value of the contrast image, corresponding to the scatter and the body thickness of the subject while the contrast image is obtained, based on the concentration of the contrast material and the thickness of the contrast material in the projection direction, in a predetermined region of the contrast image, which is obtained using the contrast material. More specifically, the acquisition function 211 estimates the scatter and the body thickness, when the curve indicating the relation between the luminance value and both the concentration and thickness of the contrast material in the contrast image satisfies the relation between the luminance value and both the concentration and thickness of the contrast material in a predetermined region. The acquisition function 211 then acquires the correction curve based on the curve corresponding to the estimated scatter and body thickness.

Figure 3:
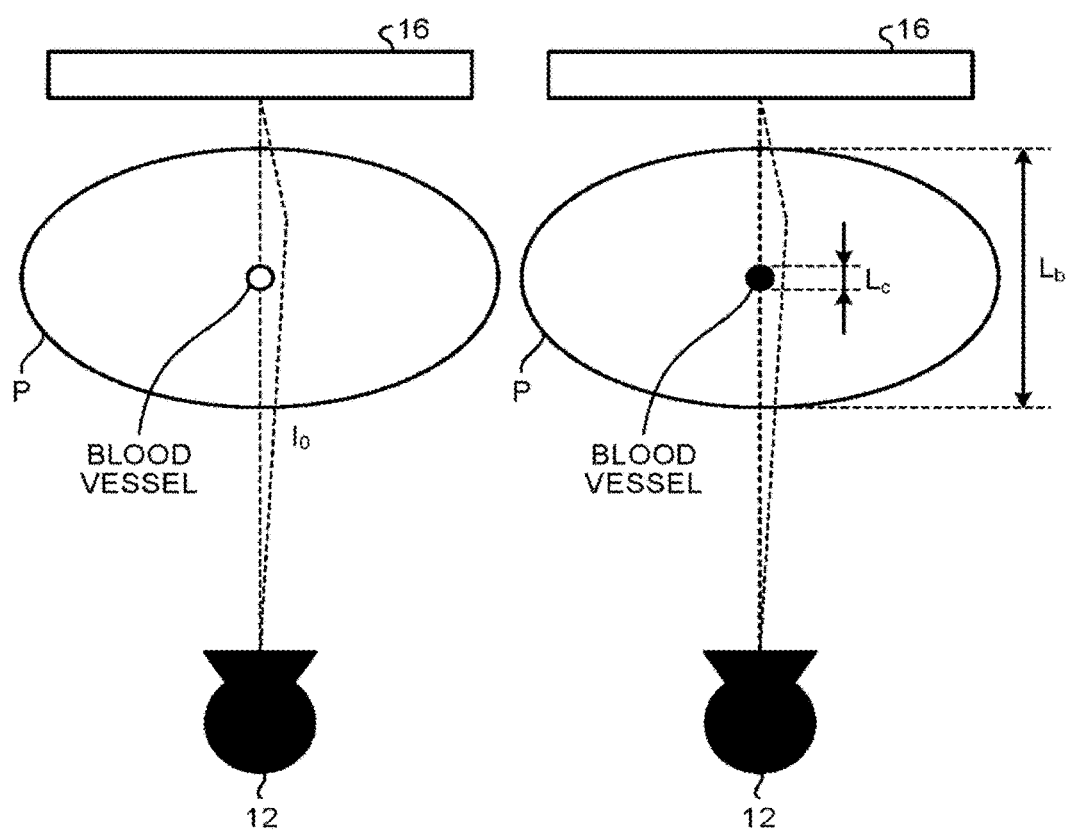
FIG. 3A is a diagram for explaining the X-ray according to the first embodiment.
FIG. 3B is a diagram for explaining the X-ray according to the first embodiment.

As described above, the curves indicating the relation between the luminance value and both the concentration and thickness of the contrast material in the differential image are curved in various ways, depending on the beam quality and the scatter while the differential image is obtained. In the actual clinical situation, the subject is human body tissues and the contrast material. Consequently, it is possible to consider that factors depending on the beam quality are the tube voltage of the X-ray tube and the body thickness of the subject. Also, the scatter changes according to the distance between the subject and the X-ray detector, and the like. Therefore, it is possible to consider that the curve indicating the relation between the concentration and thickness of the contrast material curves differently depending on the functions of the tube voltage, the body thickness, and the scatter ratio (a proportion of the scatter relative to the direct radiation). This point will now be described with reference to the following formulas (1) to (3) and FIG. 3.

FIG. 3A and FIG. 3B are diagrams for explaining the X-ray according to the first embodiment. FIG. 3A illustrates the X-ray when a mask image is obtained. FIG. 3B illustrates the X-ray when a contrast image is obtained. For example, as illustrated in FIG. 3A, "$I_0$" is the X-ray emitted from the X-ray tube 12. Thus, the luminance value of pixels corresponding to the blood vessel through which the contrast material flows in the mask image, is based on the X-ray when "$I_0$" transmits through the subject P including the blood vessel, and the scatter when "$I_0$" transmits through the subject. In other words, an X-ray "$I_B$" that reaches the X-ray detector 16 when the contrast material is not injected into the blood of the subject can be expressed as the following formula (1).

$$I_B = I_0 \times \exp(-\mu_b L_b - \mu_w L_c) + \alpha \times I_0 \times \exp(-\mu_b L_b) \quad (1)$$

In formula (1), "$\mu$" is a linear attenuation coefficient, "L" is an X-ray transmission length (thickness), and "$\alpha$" is a scatter ratio. The subscript "b" is a "body", "w" is "water", and "c" is "contrast". For example, as illustrated in formula (1), the X-ray "$I_B$" is obtained by adding "$I_0$" to the scatter "$\alpha \times I_0 \times \exp(-\mu_b L_b)$". It is to be noted that "$I_0$" is affected by the linear attenuation coefficient "$\mu_b$" of the subject's body and the body thickness "$L_b$" of the subject, as well as the linear attenuation coefficient "$\mu_w$" of the fluid (blood) in the blood vessel and the thickness "$L_c$" of the blood vessel (contrast material). It is assumed that blood and water have the same absorption properties.

Also, as illustrated in FIG. 3B, the luminance value of pixels corresponding to the blood vessel through which the contrast material flows in the contrast image, is based on the X-ray when "$I_0$" transmits through the subject P including the blood vessel through which the contrast material flows, and the scatter when "$I_0$" transmits through the subject P. In other words, an X-ray "$I_C$" that reaches the X-ray detector 16 when the contrast material is injected into the blood vessel of the subject P can be expressed as the following formula (2).

$$I_C = I_0 \times \exp(-\mu_b L_b - \mu_c L_c) + \alpha \times I_0 \times \exp(-\mu_b L_b) \quad (2)$$

In formula (2), "$\mu$" is a linear attenuation coefficient, "L" is an X-ray transmission length (thickness), and "$\alpha$" is a scatter ratio. The subscript "b" is a "body" and "c" is "contrast". For example, as illustrated in formula (2), the X-ray "$I_C$" is obtained by adding "$I_0$" to the scatter "$\alpha \times I_0 \times \exp(-\mu_b L_b)$". It is to be noted that "$I_0$" is affected by the linear attenuation coefficient "$\mu_b$" of the subject's body and the body thickness "$L_b$" of the subject, as well as the linear attenuation coefficient "$\mu_c$" of the contrast material and the thickness "$L_c$" of the blood vessel (contrast material).

The differential image obtained by performing log subtraction on the mask image and the contrast image can be expressed as the following formula (3), using formula (1) and formula (2). In formula (3), "$\tau$" is a mass attenuation coefficient and "$\rho$" is concentration. In other words, in formula (3), the linear attenuation coefficient "$\mu$" is replaced by the mass attenuation coefficient "$\tau$" and the concentration "$\rho$".

$$S = \ln\left(\frac{I_B}{I_C}\right) = \ln\left(\frac{\exp(-\mu_w L_c) + \alpha}{\exp(-\mu_c L_c) + \alpha}\right) \cong \ln\left(\frac{\exp(-\tau_w \times \rho_w \times L_c) + \alpha}{\exp(-\tau_c \times \rho_c \times L_c - \tau_w \times \rho_w \times L_c) + \alpha}\right) \quad (3)$$

As illustrated in formula (3), when formula (1) and formula (2) are differentiated by performing a logarithmic conversion thereon, a signal value (luminance value) "S" of the image is determined by the mass attenuation coefficient, the concentration, the thickness of the contrast material, and the scatter ratio. In formula (3), the mass attenuation coefficient "$\tau$" depends on the spectrum (energy) of the X-ray, and relates to the tube voltage of the X-ray tube and the body thickness of the subject. For example, the spectrum of "$I_0$" emitted from the X-ray tube 12 in FIG. 3A and FIG. 3B corresponds to the tube voltage. Hence, the spectrum of "$I_0$" changes according to the body thickness of the subject P.

If the luminance value of a region (such as a catheter region), in which the concentration and thickness of the contrast material in the actually obtained differential image are known, is applied to formula (3), unknown portions are only the scatter ratio and the body thickness of the subject, while the differential image is obtained. For example, in formula (3), the tube voltage related to "$\tau$" is the tube voltage while the differential image is obtained, and the concentration "$\rho_c$" of the contrast material is the concentration of the contrast material injected into the catheter (concentration before being diluted by blood). The thickness "$L_c$" of the contrast material is the inner diameter of the catheter, and the concentration "$\rho_w$" of fluid (blood) may be considered, for example, as "1". In other words, unknown factors in formula (3) are the body thickness of the subject related to "$\tau$", and the scatter ratio "$\alpha$".

Consequently, the X-ray diagnostic apparatus 100 according to the first embodiment measures the luminance value of a region (such as a catheter region) in which the concentration and thickness of the contrast material in the differential image are known. The X-ray diagnostic apparatus 100 then estimates the body thickness and the scatter ratio that satisfy formula (3) with the measured luminance value. The X-ray diagnostic apparatus 100 further estimates the correction curve indicating the relation between the luminance value and both the concentration and thickness of the contrast material in the target differential image, using the estimated body thickness and scatter ratio. As described above, the unknown factors in formula (3) are the body thickness of the subject and the scatter ratio. In other words, by determining the value of one factor, the value of the other factor will be determined. That is, a value corresponding to the curve indicating the relation between the luminance value and both the concentration and thickness of the contrast material in the actual differential image is included in the combination of two factors that satisfy formula (3).

Thus, the X-ray diagnostic apparatus 100 extracts the combinations of the body thickness and the scatter ratio that satisfy formula (3), and acquires the correction curve from the curves corresponding to the extracted combinations. For example, the acquisition function 211 acquires the correction curve by applying the luminance value and the known concentration and thickness of the contrast material of the catheter region to formula (3), and extracting the combinations of the body thickness and the scatter ratio. Hereinafter, processing performed by the acquisition function 211 according to the first embodiment will be described with reference to FIG. 4 to FIG. 6C. FIG. 4 to FIG. 6C are diagrams for explaining processing by the acquisition function 211 according to the first embodiment. In FIG. 4 to FIG. 6C, a correction curve that corrects the luminance value of a region besides the catheter region, such as the artery, is obtained by using the luminance value of the catheter region.

Figure 4:
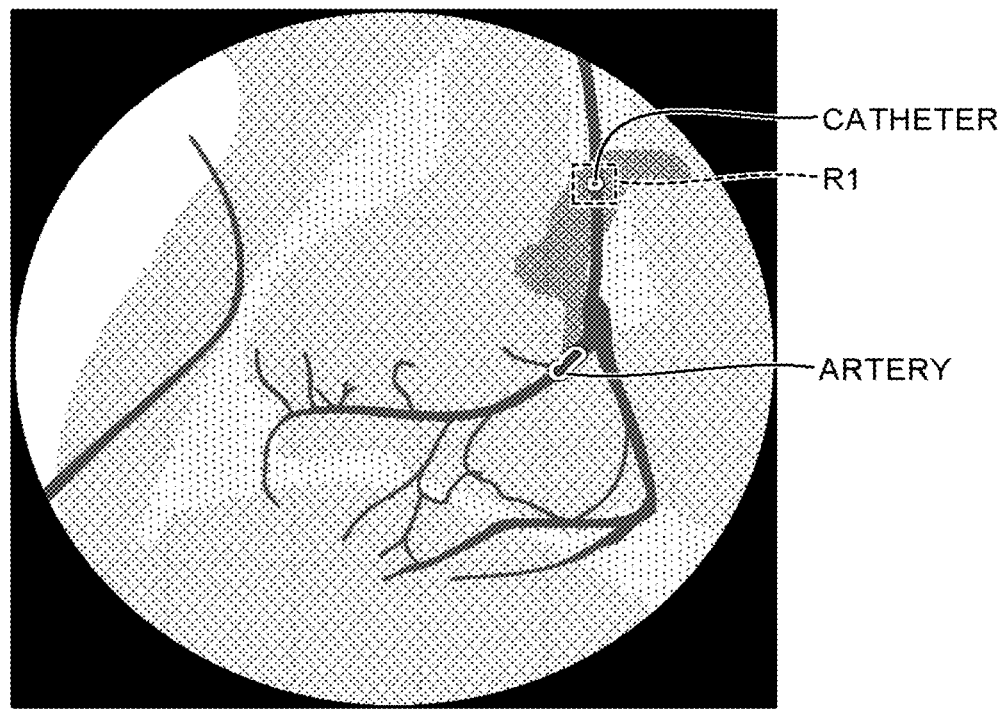
FIG. 4 is a diagram for explaining processing by an acquisition function according to the first embodiment.

For example, as illustrated in FIG. 4, the acquisition function 211 measures the luminance value in a region of interest R1 set in the catheter region specified on the differential image. For example, the region of interest R1 is set by the operator via the input circuitry 22. The acquisition function 211 estimates the scatter and the body thickness of the subject, while the contrast image is obtained, based on the luminance value at the position in which the signal from the contrast material becomes largest in a predetermined region (region in which the concentration and thickness of the contrast material are known). For example, the acquisition function 211 measures the signal intensities of the pixels along the center of the catheter in the region of interest R1, and uses the highest value among the measured signal intensities.

Figure 5:
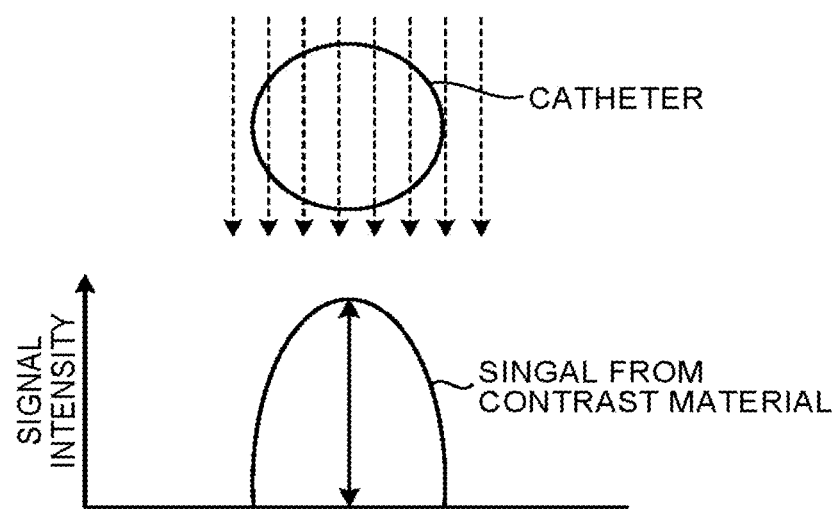
FIG. 5 is a diagram for explaining processing by the acquisition function according to the first embodiment.

FIG. 5 indicates the relation between the section of the catheter and the signal from the contrast material in the catheter. For example, when a cylindrical catheter is irradiated with the X-rays, as illustrated in FIG. 5, not only the thickest portion of the catheter but also the thin portion of the catheter is irradiated with the X-rays. At this time, the highest signal intensity of the signal from the contrast material is obtained from the thickest portion. In other words, by measuring the signal intensities of the pixels corresponding to the center of the catheter, the thickness of the contrast material becomes equivalent to the inner diameter of the catheter. Thus, it is possible to measure the luminance value of the thickest portion. Further, because the thickest portion of the catheter does not necessarily match with the signal intensities of the pixels, the acquisition function 211 measures the signal intensities of the pixels along the center of the catheter in the region of interest R1, and uses the highest value. In other words, the acquisition function 211 estimates the scatter ratio and the body thickness, by applying the luminance value corresponding to the highest signal intensity to formula (3). The concentration of the contrast material and the inner diameter of catheter may be input by the operator via the input circuitry 22, but may also be obtained from management information that uses a barcode. Today, the contrast materials and catheters used in intervention treatment are often managed with barcodes. Thus, the acquisition function 211 can acquire the information on the concentration of the contrast material and the inner diameter of the catheter currently being used, from the management information.

Figure 6A:
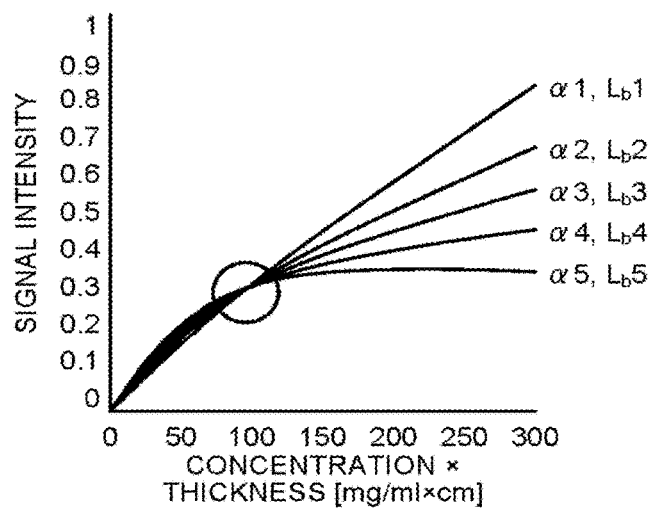
FIG. 6A is a diagram for explaining processing by the acquisition function according to the first embodiment.

When the luminance value as well as the concentration and thickness of the contrast material of the catheter region in the differential image are acquired in this manner, the acquisition function 211 applies the acquired values to formula (3) described above. With formula (3), the acquisition function 211 extracts the combinations of the scatter ratio and the body thickness that satisfy the relation between the acquired luminance value and both the concentration and thickness of the contrast material. The acquisition function 211 then acquires the correction curve from the curves corresponding to the extracted combination. For example, as illustrated in FIG. 6A, the acquisition function 211 plots the acquired value on a graph in which the vertical axis indicates the "signal intensity (luminance value)", and the horizontal axis indicates the "concentration×thickness of the contrast material (mg/ml×cm)". The acquisition function 211 then extracts the curves that pass through the plotted point.

For example, if the concentration of the contrast material is "370 (mg/ml)", the inner diameter of the catheter is "2 mm", and the signal intensity on the differential image is "0.257", as illustrated in FIG. 6A, the acquisition function 211 extracts the combinations of the scatter ratio and body thickness of $(\alpha 1, L_b 1)$, $(\alpha 2, L_b 2)$, $(\alpha 3, L_b 3)$, $(\alpha 4, L_b 4)$, and $(\alpha 5, L_b 5)$ that satisfy the relation of formula (3). The acquisition function 211 then applies the extracted combinations of the scatter ratio and body thickness to formula (3), and acquires the curves corresponding to the combinations, by changing the values of the "concentration×thickness of the contrast material". For example, the acquisition function 211 acquires the curve of $(\alpha 1, L_b 1)$ illustrated in FIG. 6A, by applying $(\alpha 1, L_b 1)$ to formula (3) and changing the value of the "concentration×thickness of the contrast material". Similarly, the acquisition function 211 acquires the curves for the other combinations.

Figure 6B:
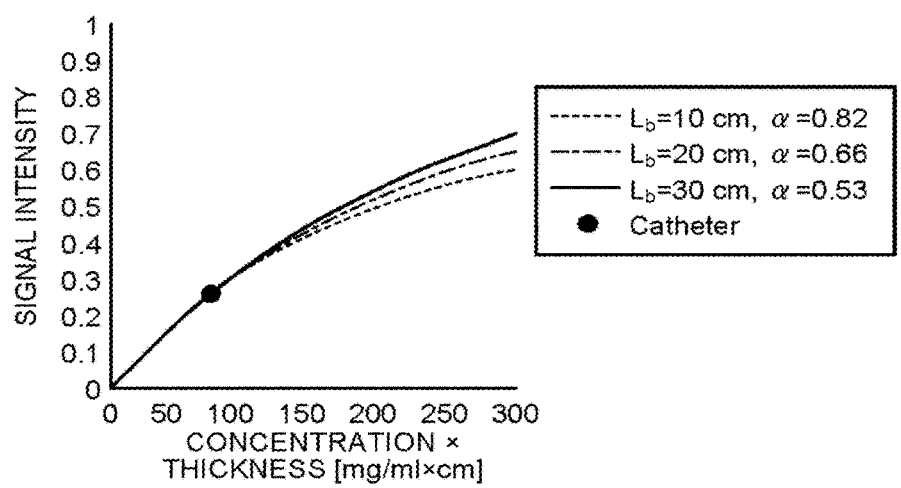
FIG. 6B is a diagram for explaining processing by the acquisition function according to the first embodiment.
Figure 6C:
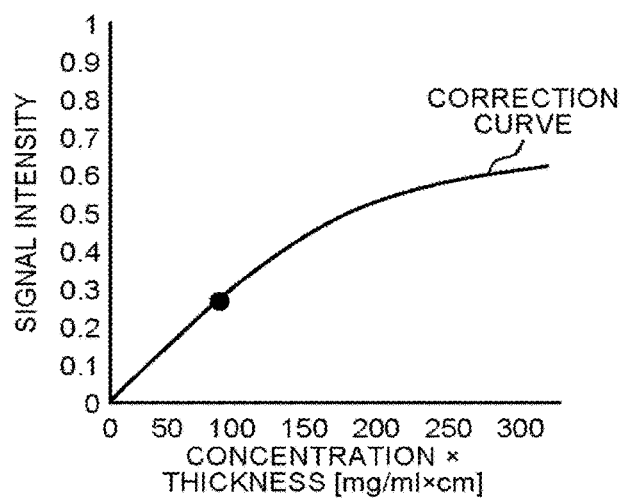
FIG. 6C is a diagram for explaining processing by the acquisition function according to the first embodiment.

The acquisition function 211 then acquires the correction curve based on the acquired curves. The acquisition function 211 estimates the scatter and the body thickness to be clinically acceptable values, and acquires the correction curve based on the curves corresponding to the estimated scatter and body thickness. For example, as illustrated in FIG. 6B, among the combinations of the scatter ratio and body thickness of $(\alpha 1, L_b 1)$, $(\alpha 2, L_b 2)$, $(\alpha 3, L_b 3)$, $(\alpha 4, L_b 4)$, and $(\alpha 5, L_b 5)$, the acquisition function 211 extracts candidate curves corresponding to the combinations of "10 cm", "20 cm", and "30 cm", which are acceptable values of the body thickness of the actual subject. For example, the acquisition function 211 acquires the correction curve as illustrated in FIG. 6C, for example, by averaging the extracted candidate curves.

For example, as illustrated in FIG. 6B, the acquisition function 211 obtains a quintic function of "$\rho_c \times L_c = 2317 \times S^5 - 2912 \times S^4 + 1610 \times S^3 - 134 \times S^2 + 255$" as the correction curve, by averaging the candidate curves corresponding to $(\alpha, L_b) = (0.82, 10 \text{ cm})$, $(0.66, 20 \text{ cm})$, and $(0.53, 30 \text{ cm})$.

Returning to FIG. 1, the correction function 212 corrects the contrast image by using the correction information acquired by the acquisition function 211. More specifically, the correction function 212 corrects the luminance value of each pixel in the contrast image, by using the correction curve. FIG. 7 is a diagram schematically illustrating processing by the correction function 212 according to the first embodiment.

For example, as illustrated in FIG. 7, the correction function 212 calculates the value of the corresponding "concentration×thickness", by applying the luminance value (signal intensity) of each pixel in the artery to the correction curve. The correction function 212 corrects the value of each pixel in the artery, by replacing the luminance value in the artery to the calculated value. Thus, it is possible to correct the luminance value in the differential image to the value that correctly reflects the "concentration×thickness of the contrast material". Consequently, for example, it is possible to accurately measure the perfusion during the intervention treatment and the like.

The correction function 212 can perform the correction processing on any region in the differential image. For example, the correction function 212 can correct the entire image, by replacing the luminance values of all the pixels in the differential image, to the value of the "concentration× thickness". The correction function 212 can also correct a part of the image, by replacing the luminance value of the pixels in a predetermined region in the differential image, to the value of the "concentration×thickness". For example, the predetermined region in the differential image includes a region (such as blood vessel and tissues) into which the contrast material flows and the like.

Figure 8A:
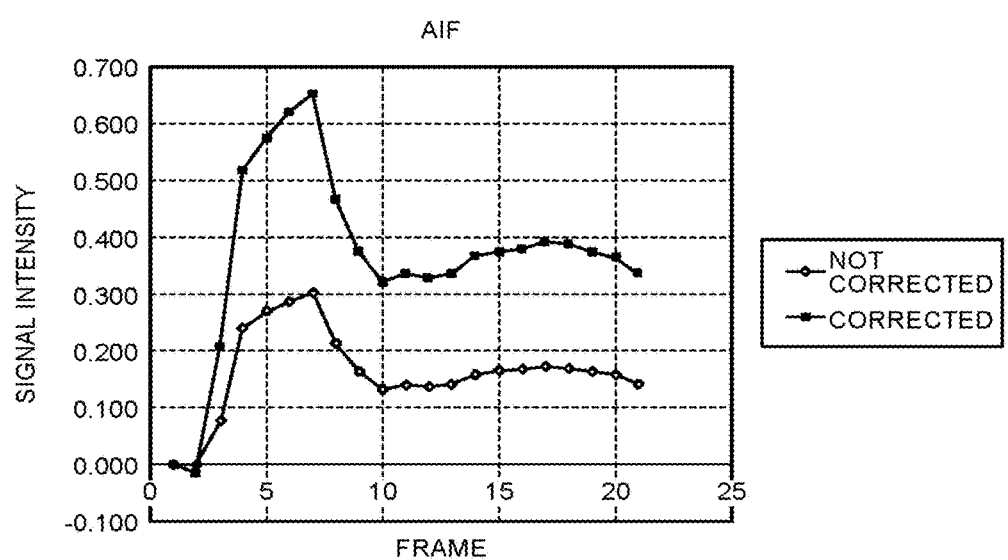
FIG. 8A is an exemplary diagram when the correction processing in the first embodiment is carried out.
Figure 8B:
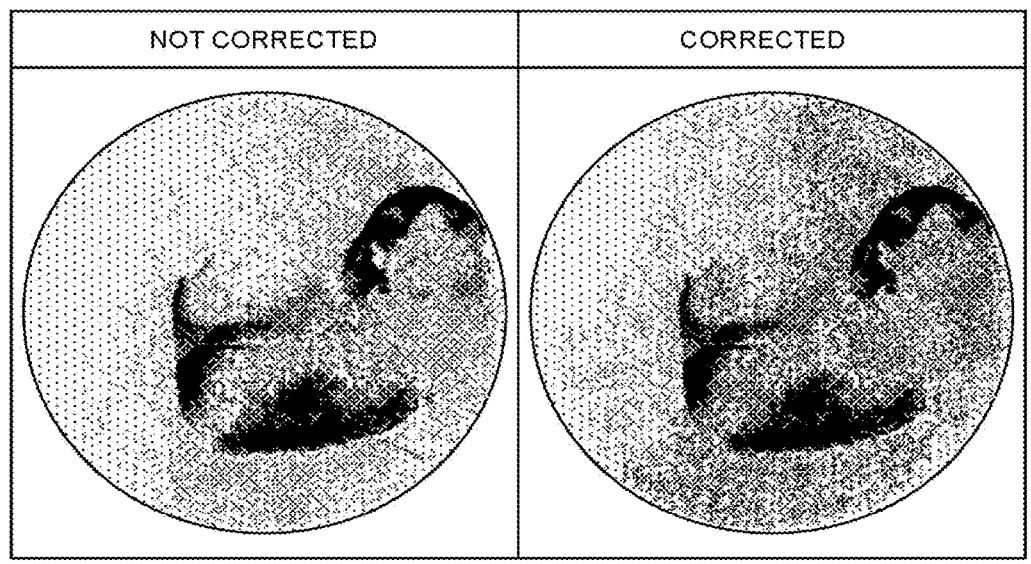
FIG. 8B is an exemplary diagram when the correction processing in the first embodiment is carried out.

As described above, by correcting the luminance value of the differential image, it is possible to accurately measure the perfusion during the intervention treatment and the like. FIG. 8A and FIG. 8B are exemplary diagrams when the correction processing in the first embodiment is carried out. In FIG. 8A and FIG. 8B, a perfusion image is generated by correcting the luminance value of each pixel in the X-ray image (frame), which is obtained by injecting the contrast material over time, with the correction described above. In FIG. 8A, the horizontal axis is the frame, and the vertical axis is the signal intensity. FIG. 8A illustrates time density curves (TDCs) obtained before and after a predetermined pixel is corrected. FIG. 8B illustrates perfusion images obtained before and after being corrected. As illustrated in FIG. 8A, by performing the correction, the signal intensity range of the TDC is increased, and it is possible to further reflect the difference in the concentration of contrast material on the difference in signal intensity. Also, as illustrated in FIG. 8B, it is possible to generate a perfusion image that further reflects the flowing state of the contrast material, by performing the correction.

As described above, the X-ray diagnostic apparatus 100 according to the first embodiment performs the correction processing on the luminance value and the concentration of the contrast material, by only using the differential image. If the inner diameter of catheter is used as the thickness of the contrast material, the longitudinal direction of the catheter needs to be orthogonal to the irradiation direction of the X-rays (image projection direction). In other words, if the catheter is not orthogonal to the projection direction (tilted), the thickness of the contrast material is not the inner diameter of the catheter, but the thickness of the contrast material in the projection direction when the catheter is tilted.

Figure 9A:
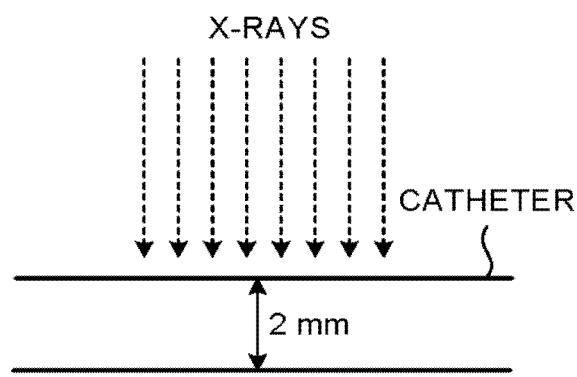
FIG. 9A is a diagram for explaining an example of processing by a calculation function according to the first embodiment.
Figure 9B:
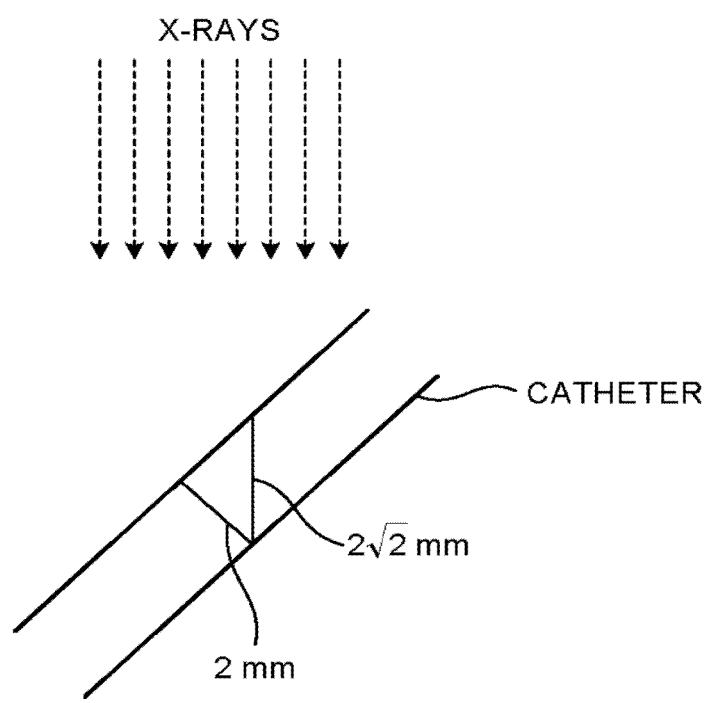
FIG. 9B is a diagram for explaining an example of processing by the calculation function according to the first embodiment.

In the X-ray diagnostic apparatus 100 according to the first embodiment, the calculation function 213 first determines whether the catheter is tilted. If the catheter is tilted, the calculation function 213 calculates the thickness of the contrast material in the projection direction. More specifically, the calculation function 213 calculates the thickness of the contrast material in the projection direction, based on the angle formed by the longitudinal direction of the catheter and the projection direction. FIGS. 9A and 9B are diagrams for explaining an example of processing by the calculation function 213 according to the first embodiment. For example, if the catheter having the inner diameter of "2 mm" illustrated in FIG. 9A is tilted toward the irradiation direction of the X-rays (projection direction) by 45 degrees, as illustrated in FIG. 9B, the calculation function 213 calculates the thickness "2√2" of the catheter in the direction parallel to the projection direction, and sets the calculated "2√2" as the thickness of the contrast material.

The angle (inclination of the catheter) formed by the longitudinal direction of the catheter and the projection direction can be calculated by using biplane imaging or a distance marker on the catheter. For example, the biplane imaging not only obtains a differential image from the aiming direction, but also obtains a differential image from the direction orthogonal to the aiming direction. The calculation function 213 then measures the inclination relative to the vertical direction (or horizontal direction) of the catheter included in the differential image, which is obtained from the orthogonal direction. The calculation function 213 then sets the measured inclination as the inclination of the catheter in the differential image obtained from the aiming direction.

The calculation function 213 also calculates the inclination of the catheter, based on the changes of the distance marker on the catheter provided at a predetermined interval. For example, if the catheter to be used is marked at "10 mm" intervals, and if the interval of the distance marker included in the mask image corresponds to the interval of "10 mm", the calculation function 213 determines that the catheter is not tilted. On the other hand, if the interval of the distance marker included in the mask image does not correspond to the interval of "10 mm", the calculation function 213 determines that the catheter is tilted, and calculates the inclination of the catheter. For example, if the interval of the distance marker included in the mask image corresponds to "8 mm", the calculation function 213 calculates the inclination of the catheter "θ"="$\cos^{-1} 8/10$".

The calculation function 213 then calculates the thickness of the contrast material by using the calculated inclination (angle) of the catheter. The acquisition function 211 applies the thickness of the contrast material calculated by the calculation function 213 to formula (3), and acquires the correction curve.

The processing performed by the X-ray diagnostic apparatus 100 according to the first embodiment will now be described with reference to FIG. 10. FIG. 10 is a flowchart illustrating a processing procedure of the X-ray diagnostic apparatus 100 according to the first embodiment. In FIG. 10, the input circuitry 22 executes step S101. At step S101, the input circuitry 22 receives a setting operation of a region (such as a catheter region), in which the concentration and thickness of the contrast material are known, from the operator. At step S102, the processing circuitry 21 reads out the program corresponding to the acquisition function 211 from the storage circuitry 25 and executes the program. At step S102, the processing circuitry 21 acquires the concentration and thickness of the contrast material in the region.

At steps S103 and S104, the processing circuitry 21 reads out the program corresponding to the calculation function 213 from the storage circuitry 25 and executes the program. At step S103, the processing circuitry 21 determines whether the catheter is tilted. If it is determined that the catheter is tilted (Yes at step S103), at step S104, the processing circuitry 21 corrects the thickness based on the angle. If it is determined that the catheter is not tilted (No at step S103), the processing circuitry 21 does not execute step S104.

At steps S105 and S106, the processing circuitry 21 reads out the program corresponding to the acquisition function 211 from the storage circuitry 25 and executes the program. At step S105, the processing circuitry 21 estimates candidate curves from the luminance value and both the concentration and thickness of the contrast material in the region. At step S106, the processing circuitry 21 derives a correction curve from the candidate curves, by performing processing such as averaging the candidate curves.

At step S107, the processing circuitry 21 reads out the program corresponding to the correction function 212 from the storage circuitry 25, and executes the program. At step S107, the processing circuitry 21 corrects the contrast image using the correction curve.

As described above, in the first embodiment, the acquisition function 211 acquires correction information on the luminance value of a contrast image corresponding to the scatter and the body thickness of the subject, while the contrast image is obtained, based on the concentration of the contrast material and the thickness of the contrast material in the projection direction in a predetermined region of the contrast image, which is obtained using the contrast material. By using the correction information, the correction function 212 corrects the contrast image. Thus, the X-ray diagnostic apparatus 100 according to the first embodiment can perform correction by only using the contrast material, thereby enabling to easily correct the contrast image. Because only the contrast image is used for the correction, it is also possible to correct the contrast image that is already obtained.

According to the first embodiment, the acquisition function 211 estimates the scatter and the body thickness, when the curve indicating the relation between the luminance value and both the concentration and thickness of the contrast material in the contrast image satisfies the relation between the luminance value and both the concentration and thickness of the contrast material in a predetermined region. The acquisition function 211 then acquires the correction curve based on the curves corresponding to the estimated scatter and body thickness. The correction function 212 corrects the luminance value of pixels in the contrast image by using the correction curve. Thus, the X-ray diagnostic apparatus 100 according to the first embodiment enables the correction in which the scatter and the body thickness, which are factors that change the curve indicating the relation between the luminance value and both the concentration and thickness of the contrast material in the contrast image, are taken into account.

According to the first embodiment, the acquisition function 211 estimates the scatter and the body thickness to be clinically acceptable values, and acquires the correction curve based on the curves corresponding to the estimated scatter and body thickness. According to the first embodiment, the acquisition function 211 acquires the correction curve by averaging the curves that satisfy the relation between the luminance value and both the concentration and thickness of the contrast material in a predetermined region. Thus, the X-ray diagnostic apparatus 100 according to the first embodiment enables the accurate correction.

According to the first embodiment, the acquisition function 211 estimates the scatter and the body thickness of the subject while the contrast image is obtained, based on the luminance value of the position in which the signal from the contrast image becomes maximum in a predetermined region. Thus, the X-ray diagnostic apparatus 100 according to the first embodiment enables the correction using the highly accurate portion of the correction curve. For example, as illustrated in FIG. 6B, when the candidate curves that indicate the relation between the luminance value and both the concentration and thickness of the contrast material in the differential image are to be extracted, portions of the curves below the point, in which the relation between the luminance value and both the concentration and thickness of the contrast material in the catheter is plotted, and where the "concentration×thickness" is low, are curved similarly. On the other hand, the curves above the point, in which the relation between the luminance value and both the concentration and thickness of the contrast material in the catheter is plotted, and where the "concentration×thickness" is high, are curved differently.

In other words, when the correction curve is calculated by averaging the candidate curves, errors that occur due to averaging are reduced at the portion below the point, in which the relation between the luminance value and both the concentration and thickness of the contrast material in the catheter is plotted. The errors are increased at the portions above the point, in which the relation between the luminance value and both the concentration and thickness of the contrast material in the catheter is plotted. Thus, during the correction processing, it is possible to correct more accurately, when the portion of the correction curve below the plotted point is used. Consequently, by plotting the point at which the signal intensity is increased, the portion of the correction curve below the plotted point is increased. Hence, it is possible to more accurately correct the contrast image.

According to the first embodiment, the predetermined region is the catheter region included in the contrast image. The acquisition function 211 uses the concentration of the contrast material to be injected through the catheter, and the inner diameter of the catheter, as the concentration and the thickness of the contrast material in the predetermined region. Thus, the X-ray diagnostic apparatus 100 according to the first embodiment can easily acquire the concentration and thickness of the contrast material.

According to the first embodiment, the calculation function 213 calculates the thickness of the contrast material in the projection direction, based on the angle formed by the longitudinal direction of the catheter and the projection direction. The acquisition function 211 uses the thickness of the contrast material calculated by the calculation function 213, as the thickness of the contrast material in the predetermined region. Hence, the X-ray diagnostic apparatus 100 according to the first embodiment can accurately perform the correction processing even if the catheter is tilted.

According to the first embodiment, the calculation function 213 calculates the angle formed by the longitudinal direction of the catheter and the projection direction, based on the contrast image of the catheter obtained at least from two directions, or based on the distance marker on the catheter. Thus, the X-ray diagnostic apparatus 100 according to the first embodiment can easily calculate the inclination of the catheter.

Second Embodiment

In the embodiment described above, the correction curve is acquired by estimating the scatter ratio and the body thickness, from the luminance value and both the concentration and thickness of the contrast material. In the second embodiment, correction curves are stored in advance, and a correction curve is selected from the luminance value and both the concentration and thickness of the contrast material. The X-ray diagnostic apparatus 100 according to the second embodiment is different from the X-ray diagnostic apparatus 100 according to the first embodiment, in information stored in the storage circuitry 25 and the processing ratio of the acquisition function 211. These will now be described.

Figure 11:
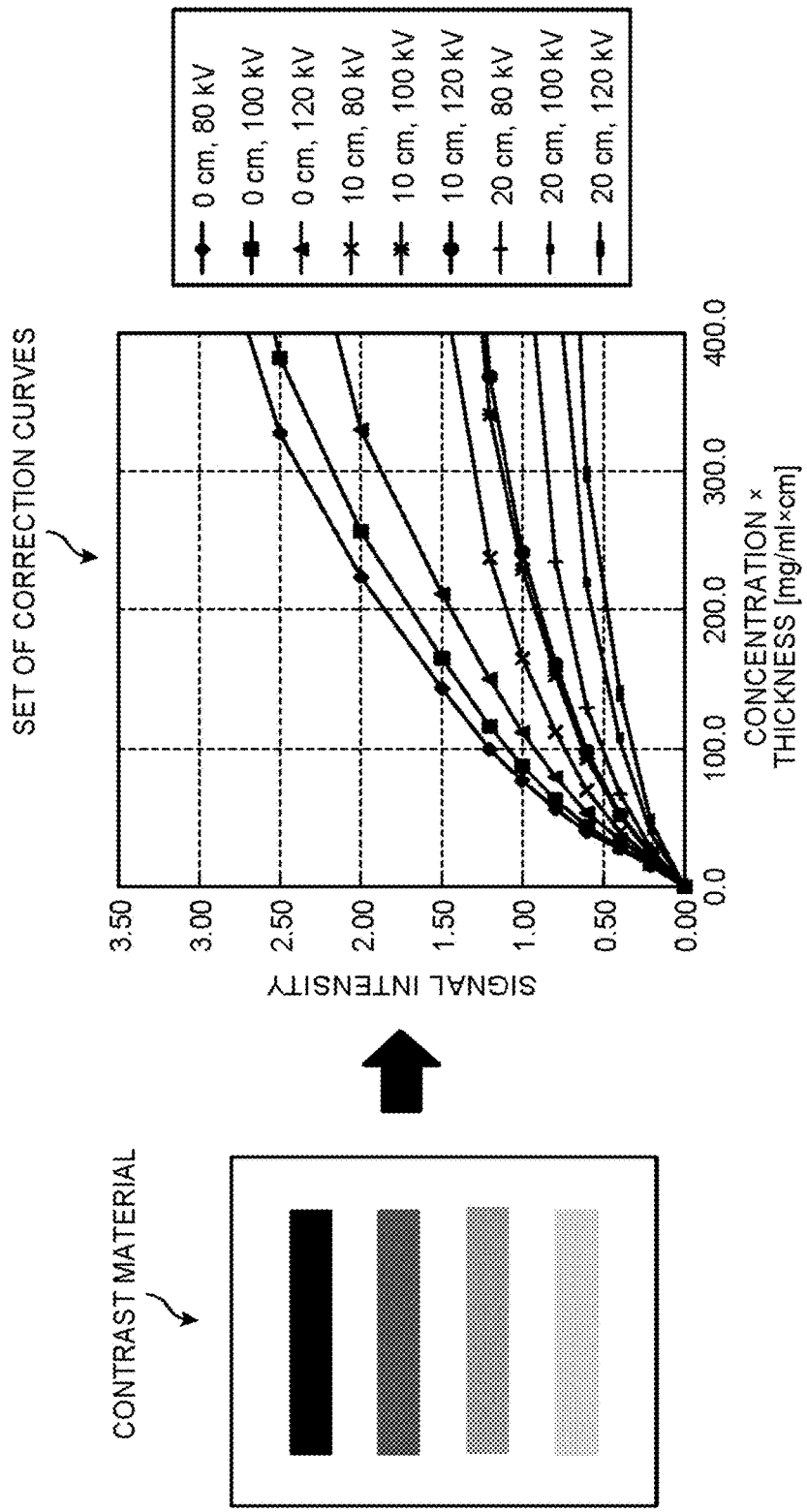
FIG. 11 is a diagram schematically illustrating information stored in storage circuitry according to a second embodiment.

FIG. 11 is a diagram schematically illustrating information stored in the storage circuitry 25 according to the second embodiment. For example, as illustrated in FIG. 11, the storage circuitry 25 stores therein the correction curves (or candidate curves) calculated using contrast materials with various concentrations. For example, the contrast materials illustrated in FIG. 11 have constant thickness and various concentrations. By capturing images of the contrast materials under various conditions, a set of correction curves as illustrated in FIG. 11 is obtained, and the storage circuitry 25 stores therein the acquired set of correction curves. For example, the correction curves are acquired by changing the conditions such as the tube voltage and the thickness of the subject, and are stored in the storage circuitry 25.

The acquisition function 211 extracts a curve that satisfies the relation between the luminance value and both the concentration and thickness of the contrast material in a predetermined region, from the curves that indicate the relation between the luminance value and both the concentration and thickness of the contrast material in the contrast image, which is set in advance for each condition of the scatter and the body thickness. The acquisition function 211 then acquires the correction curve based on the extracted curve. For example, when the luminance value and both the concentration and thickness of the contrast material in the catheter region are acquired, the acquisition function 211 acquires a curve that satisfies the acquired values from the set of correction curves. If a multiple number of curves are obtained, the acquired curves may be averaged.

As described above, according to the second embodiment, the acquisition function 211 extracts a curve that satisfies the relation between the luminance value and both the concentration and thickness of the contrast material in a predetermined region, from the curves that indicate the relation between the luminance value and both the concentration and thickness of the contrast material in the contrast image, which is set in advance for each condition of the scatter and the body thickness. The acquisition function 211 then acquires the correction curve based on the extracted curve. The correction function 212 corrects the luminance value of the pixels in the contrast image by using the correction curve. Thus, the X-ray diagnostic apparatus 100 according to the second embodiment can correct the contrast image with simple processing.

Third Embodiment

While the first and second embodiments have been described, it is to be understood that various other modifications may be made in addition to the first and second embodiments described above.

In the first embodiment described above, the catheter region is used as a region in which the concentration and thickness of the contrast material are known. However, the embodiment is not limited thereto, and for example, three-dimensional image data may also be used. For example, the three-dimensional image data is often acquired in advance to carry out the intervention treatment. Thus, it is possible to acquire the thickness from the three-dimensional image data and use the acquired thickness. For example, the thickness of the contrast material in the differential image can be obtained; by positioning the target blood vessel, which is included in the image data obtained in advance using the contrast material, on the blood vessel in the differential image in an overlapping manner; and measuring the thickness of the blood vessel in the projection direction in the differential image, using the three-dimensional image. It is also possible to use the concentration of the contrast material before being diluted, by injecting the contrast material at the position in which the thickness of the blood vessel is measured.

In the embodiment described above, the X-ray diagnostic apparatus executes the processing. However, the embodiment is not limited thereto, and for example, the processing described above may be executed by an image processing apparatus. In such a case, the storage circuitry 25 and the processing circuitry 21 described above are included in the image processing apparatus, so as to execute each processing described above.

Each of the constituent elements of each apparatus illustrated in the first embodiment is functionally conceptual, and need not necessarily be physically configured as illustrated in the drawings. In other words, the specific mode of dispersion and integration of each apparatus is not limited to the ones illustrated in the drawings, and all or a part thereof can be functionally or physically distributed or integrated in an optional unit, depending on various kinds of loads and the status of use. Moreover, all or an optional part of the processing functions carried out in each apparatus can be implemented by a CPU and a computer program analyzed and executed by the CPU, or can be implemented as hardware by the wired logic.

As described above, according to the X-ray diagnostic apparatus of at least one of the embodiments can easily correct the contrast image.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processing apparatus, comprising:
processing circuitry configured to
acquire correction information on a luminance value of a contrast image, based on a concentration of a contrast material and a thickness of the contrast material in a projection direction in a device that is inserted into a blood vessel, in the contrast image, and
correct the contrast image using the acquired correction information.

2. The image processing apparatus according to claim 1, wherein the processing circuitry is further configured to
estimate scatter and body thickness, when a curve that indicates a relation between the luminance value and both the concentration and the thickness of the contrast material in the contrast image, satisfies a relation between the luminance value and both the concentration and the thickness of the contrast material in a predetermined region, and acquire a correction curve based on the curve that corresponds to the estimated scatter and the body thickness, and
correct the luminance value of each pixel in the contrast image using the acquired correction curve.

3. The image processing apparatus according to claim 2, wherein the processing circuitry is further configured to estimate each of the scatter and the body thickness to be a clinically acceptable value, and acquire the correction curve based on the curve corresponding to the estimated scatter and the body thickness.

4. The image processing apparatus according to claim 1, wherein the processing circuitry is further configured to
extract a curve that satisfies a relation between the luminance value and both the concentration and the thickness of the contrast material in the predetermined region, from a plurality of curves that each indicates a relation between the luminance value and both the concentration and the thickness of the contrast material in the contrast image that is set in advance for each condition of the scatter and the body thickness, and acquire the correction curve based on the extracted curve, and
correct the luminance value of each pixel in the contrast image using the acquired correction curve.

5. The image processing apparatus according to claim 2, wherein the processing circuitry is further configured to acquire the correction curve by averaging the curves that each satisfies the relation between the luminance value and both the concentration and the thickness of the contrast material in the predetermined region.

6. The image processing apparatus according to claim 3, wherein the processing circuitry is further configured to acquire the correction curve by averaging the curves that each satisfies the relation between the luminance value and both the concentration and the thickness of the contrast material in the predetermined region.

7. The image processing apparatus according to claim 2, wherein the processing circuitry is further configured to estimate the scatter and the body thickness of a subject while the contrast image is obtained, based on a luminance value at a position in which a signal from the contrast material becomes maximum in the predetermined region.

8. The image processing apparatus according to claim 3, wherein the processing circuitry is further configured to estimate the scatter and the body thickness of a subject while the contrast image is obtained, based on a luminance value at a position in which a signal from the contrast material becomes maximum in the predetermined region.

9. The image processing apparatus according to claim 2, wherein
the predetermined region is a catheter region included in the contrast image, and
the processing circuitry is further configured to use the concentration of the contrast material, which is injected through a catheter, and an inner diameter of the catheter, as the concentration and the thickness of the contrast material in the predetermined region.

10. The image processing apparatus according to claim 3, wherein
the predetermined region is a catheter region included in the contrast image, and
the processing circuitry is further configured to use the concentration of the contrast material, which is injected through a catheter, and an inner diameter of the catheter, as the concentration and the thickness of the contrast material in the predetermined region.

11. The image processing apparatus according to claim 9, wherein the processing circuitry is further configured to
calculate the thickness of the contrast material in the projection direction, based on an angle formed by a longitudinal direction of the catheter and the projection direction, and
use the calculated thickness of the contrast material as the thickness of the contrast material in the predetermined region.

12. The image processing apparatus according to claim 10, wherein the processing circuitry is further configured to
calculate the thickness of the contrast material in the projection direction, based on an angle formed by a longitudinal direction of the catheter and the projection direction, and
use the calculated thickness of the contrast material as the thickness of the contrast material in the predetermined region.

13. The image processing apparatus according to claim 11, wherein the processing circuitry is further configured to calculate the angle formed by the longitudinal direction of the catheter and the projection direction, based on the contrast image of the catheter, which is from at least two directions, or a distance marker on the catheter.

14. The image processing apparatus according to claim 12, wherein the processing circuitry is further configured to calculate the angle formed by the longitudinal direction of the catheter and the projection direction, based on the contrast image of the catheter, which is obtained from at least two directions, or a distance marker on the catheter.

15. An X-ray diagnostic apparatus, comprising:
processing circuitry configured to
acquire correction information on a luminance value of a contrast image, based on a concentration of a contrast material and a thickness of the contrast material in a projection direction in a device that is inserted into a blood vessel, in the contrast image, and
correct the contrast image using the acquired correction information.

* * * * *